United States Patent [19]

Kuroda et al.

[11] Patent Number: 5,773,688

[45] Date of Patent: Jun. 30, 1998

[54] GENE EXPRESSION VECTOR USING THE GENE EXPRESSION REGULATING REGION OF THE ADP RIBOSYLATION FACTOR

[75] Inventors: Hisao Kuroda; Naohiko Hirota; Kazutoshi Ito, all of Gunma-ken, Japan

[73] Assignee: Sapporo Breweries Limited, Tokyo, Japan

[21] Appl. No.: 418,444

[22] Filed: Apr. 7, 1995

[30] Foreign Application Priority Data

Apr. 8, 1994 [JP] Japan ..................................... 6-071048

[51] Int. Cl.⁶ .......................... C12N 15/82; C12N 15/63; C07H 21/04; A01H 5/00
[52] U.S. Cl. ....................... 800/205; 435/320.1; 435/421; 536/241
[58] Field of Search ................................. 435/320.1, 421; 536/24.1; 800/205

[56] References Cited

PUBLICATIONS

Kim et al. A 20 nucleotide upstream element is essential for the nopaline synthase (nos) promoter activity. Plant Molecular Biology 24:105–117, 1994.
Serventi, et al. Characterization of the gene for ADP–ribosylation factor (ARF) 2, a developmentally regulated, selectively expressed member of the ARF family of ~20–kDa guanine nucleotide–binding proteins. The Journal of Biological Chemistry. 266(7):4, 1993.

Randy S. Haun et al., "Characterization of the Human ADP–Ribosylation Factor 3 Promoter", The Journal of Biological Chemistry, vol. 268, No. 1, pp. 8793–8800, Apr. 25, 1993.
Febs Letters, vol. 316, No. 2, pp. 133–136, 1993, F. Regad, et al., "CDNA Cloning and Expression of an Arabidopsis GTP–Binding Protein of the ARF Family".
Journal of Biological Chemistry, vol. 268, No. 7, pp. 4863–4872, Mar. 5, 1993, I.M. Serventi, et al., "Characterization of the Gene for ADP–Ribosylation Factor (ARF) 2, A Developmentally Regulated Selectively Expressed Member of the ARF Family of ~20–KDA Guanine Nucleotide–Binding Proteins".
The EMBO Journal, vol. 9, No. 6, pp. 1677–1684, 1990, Philip N. Benfey, et al., "Tissue–Specific Expression from CaMV 35s Enhancer Subdomains in Early Stages of Plant Development".
The Plant Cell, vol. 2, pp. 163–171, Feb. 1990, David McElroy, et al., "Isolation of an Efficient Actin Promoter for Use in Rice Transformation".

*Primary Examiner*—Douglas W. Robinson
*Assistant Examiner*—Thanda Wai
*Attorney, Agent, or Firm*—Oblon, Spivak, McClelland, Maier & Neustadt, P.C.

[57] ABSTRACT cDNA derived from the ARF gene that is actively expressed in barley seeds, roots and callus, but is highly suppressed or almost not expressed at all in leaves, was cloned. Next, the upstream region of the ARF gene was cloned, its promoter activity was verified, and a gene expression vector using the expression region of this gene was produced.

7 Claims, 3 Drawing Sheets

|     | 10 | 20 | 30 | 40 | 50 | 60 |
|---|---|---|---|---|---|---|
| Barley ARF | MGLTFTKLFS | RLFAKKEMRI | LMV`GLDAAGK` | TTILYKLKLG | EIVTTIPTIG | FNVETVEYKN |
| Human ARF3 | --NI-GN-LK | S-IG------ | ---------- | ---------- | ---------- | ---------- |
| Human ARF1 | --NI-AN--K | G--G------ | ---------- | ---------- | ---------- | ---------- |
| Bovine ARF1 | --NI-AN--K | G--G------ | ---------- | ---------- | ---------- | ---------- |
| Bovine ARF2 | --NV-E---K | S--G------ | ---------- | ---------- | ---------- | ---------- |
| Yeast ARF | ---FA----S | N--GN----- | -----G---  | --V------- | -VI------- | ------Q--- |

|     | 70 | 80 | 90 | 100 | 110 | 120 |
|---|---|---|---|---|---|---|
| Barley ARF | ISFTVW`DVGG` | QDKIRPLWRH | YFQNTQGLIF | VVDSNDRDRV | VEARDELHRM | LNEDELRDAV |
| Human ARF3 | ---------- | ---------- | ---------- | -------E-- | N---E--M-- | -A-------- |
| Human ARF1 | ---------- | ---------- | ---------- | -------E-- | N---E--M-- | -A-------- |
| Bovine ARF1 | ---------- | ---------- | ---------- | -------E-- | N---E--M-- | -A-------- |
| Bovine ARF2 | ---------- | ---------- | ---------- | -------E-- | N---E--T-- | -A-------- |
| Yeast ARF | ---------- | --R--S---- | -YR--E-V-- | -------S-I | G---EVMQ-- | -------N-A |

|     | 130 | 140 | 150 | 160 | 170 | 181 |
|---|---|---|---|---|---|---|
| Barley ARF | LLVFA`NKQDL` | PNAMNAAEIT | DKLGLHSLRQ | RHWYIQSTCA | TTGEGLYEGL | DWLSSNIANKS |
| Human ARF3 | ---------- | ---------- | ---------H | -N----A--- | -S-D------ | ---ANQLK--K |
| Human ARF1 | ---------- | ---------- | ---------H | -N----A--- | -S-D------ | ----NQLR-QK |
| Bovine ARF1 | ---------- | ---------- | ---------H | -N----A--- | -S-D------ | ----NQLR-QK |
| Bovine ARF2 | ----V----- | ---------- | ---------- | -N----A--- | -S-D------ | ----NQLK-QK |
| Yeast ARF | W--------- | -E--S----- | E------I-N | -P-F--A--- | -S-------- | E---NSLK-ST |

Homology of barley ARF (R151) with human, bovine and yeast ARF

*FIG. 1*

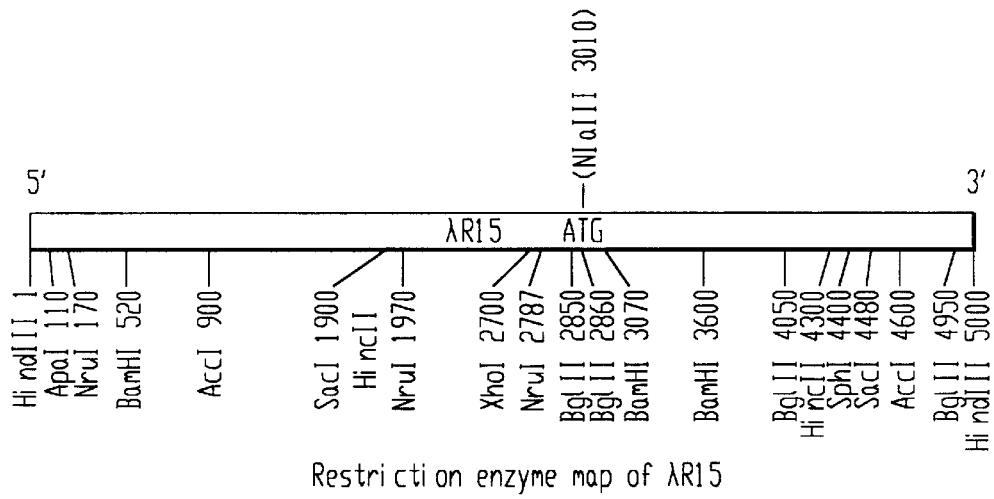

Restriction enzyme map of λR15

*FIG. 2*

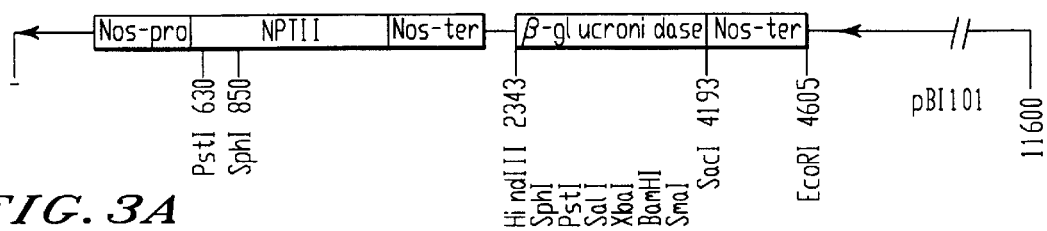
*FIG. 3A*
Hind III-EcoRI, 2280 fragment of
pBI101 ligated to Hind III-EcoRI
site of pUC118
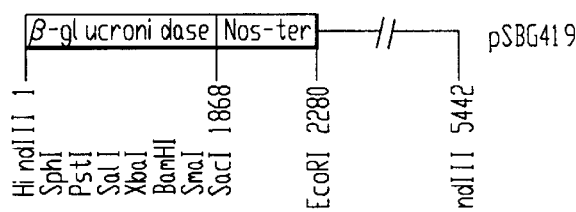
*FIG. 3B*
Blunting of PstI site
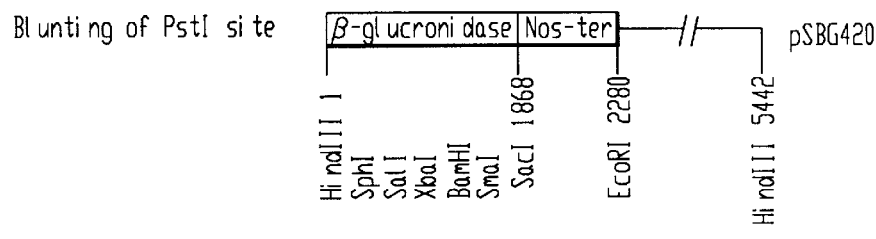
*FIG. 3C*
Insertion of R15 promoter fragment at Hind III site
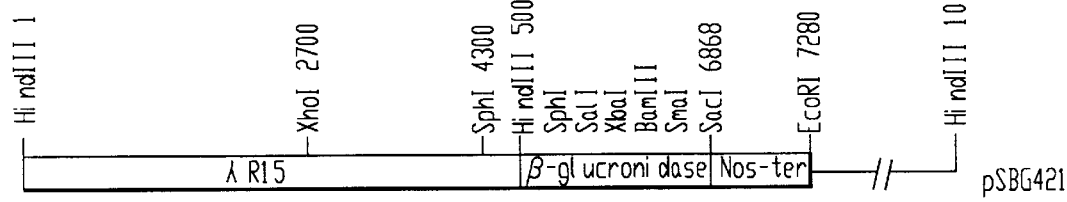
*FIG. 3D*
Exchange of pSBG421 XhoI(2700)-SphI(5000) and λR15XhoI(2700)-
NlaIII(3010) fragments
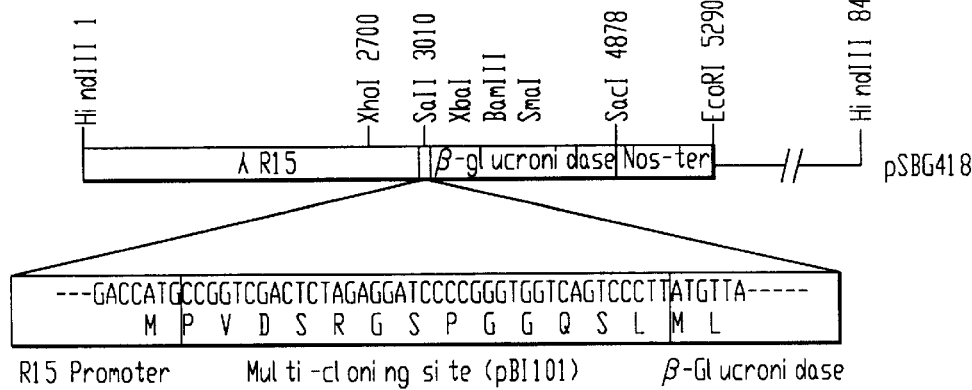
*FIG. 3E* construction of pSBG418

Analysis of R15 promoter activity

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
      ( A ) LENGTH: 3088 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:1:

```
AAGCTTCTAG   ATCACCGAAG   ATGGGCCAGA   GGGGGGCCAG   GGGCTGCCCA   GGCGCCCTGC       60

TGGCGTGGCC   AGGCCCTAGG   CCGCGCCAGG   AGGCCGCCTG   GGTGGGCCCC   ACCTCCTCCG      120

GTGCCCTCCT   TTGGCCTATA   TTTAGAGTCC   CGAGAGGAAA   CCCTTCCACA   ACTTCCAGAA      180

TCGCGAATTT   CTCCATCGTT   CCGTTGCCGC   AGCGCTTCCG   AGATCGGGAG   CGTCAGGAGA      240

CCTCTTCCCG   ATACCCTGCC   GGAGGGAGGA   TTGACCTTCG   GGAGCTTCTC   CACCGCAATC      300

AACGCTTCCC   GGACGTGCCG   TGAGTAGTCC   TCCTTGGACC   ATGGGTCCAT   GACCAGTAAC      360

TATGTGATGT   CTTCTCTCCA   ATCTTGTGCT   TCATTGGTTA   GTCCTTGTGA   GCTGCCCTAC      420

ATGATCAAGG   CATCTATGTA   ATTCTCTTGC   TATTGCTATG   CTCGGTTTGT   TGGGATCCGA      480

TGAATTATGA   GATTATGTTC   AGATTGTTAT   GAGTTATATA   TTTGATTATC   CTTTTATATA      540

ACGTTTCTTA   GTGATTCATG   CATGTTCTCT   ATTGCTATTT   ATTGCTTTGG   TCGAGTAGTA      600

GATTGTAACT   CCAAGAGGGA   GCGTTATGCA   TGATTATGGG   TTCATGCCCC   TCGATGTCTT      660
```

| | | | | | |
|---|---|---|---|---|---|
| GCTTGAGTGA | CATGAACATG | AGACTAGGGG | ATGTGCTGTT | GCCACCAGGG | AGAAAAAAAT | 720
| GATGCTTGTG | ACCTCAGTTG | CAAGGATTAT | TTACCTCACA | CATAGTTCGT | TAATGAAGTT | 780
| GTCCGTTACT | TTGAGTTTAC | ACTTTGGATG | GGGCTCGCAA | CTTAATACCG | GAGAGATGTT | 840
| CTGGATAGAT | ATCTCAAGGT | GGATGATTAG | TAAGTAGATG | CTGATGAATA | AACGGTCTAC | 900
| TTGTCTTGAC | GTACTGCCCA | TTACTATTGA | GCCTATAACT | ATCAAGTAGC | ATAATTAGCA | 960
| TTGTGGTGCG | TTCATAATTC | TGTCAATTGC | CCAACTGTGA | TTTGTTATC | ATAGCATAGT | 1020
| TGTTTATCGT | CTTTTGGAAG | AGATACATCA | CTAGTGAACA | TCATGTGACA | CCGGTCAATA | 1080
| TCACCACCAT | TGTTACACA | TCCATCATTT | ACCGCTTTCA | TTTACTTTTC | CGTTGCAATC | 1140
| ACTATTACCT | TCCCGCTTGT | GTTTTGATCC | TTTGCAAACT | ACAAGGTCGG | AGAGATTGGC | 1200
| AACCTCTCTG | TACTCGTTGG | GAGCAAAGTT | ATTTGTTGTG | TGTGCAGGTC | CACGTCTTCT | 1260
| ACTGACCAGA | ACAGGAGACA | CCTACTTGTT | GGTCCTACGA | GTCCTCTTGG | TTTGTTAAAC | 1320
| CTTACAGTTC | CCGTGTGAGG | AAAAACTTGT | TGCTGATTAC | ATCTCAACAT | TTCACTTTGG | 1380
| GTAATCAACT | AGGTGCGAGA | AATATATATA | CATCTCTCGT | CATCAAAAGG | CGAAAGTTAT | 1440
| TTTATTATCT | CATTAAAAGT | TTCAAAAAAT | TTAAATTCCA | CTCAATTCCA | ATCAATCACT | 1500
| CAAGCAAGCA | AAACATATAA | TTGATTATTA | TAACATTTCA | TTTTTTGGGA | TGTTACATGA | 1560
| TTCATGTTAT | GGGTTAGAGT | TATCTTAATT | CTTCTTTCAT | AGTTGCGAAT | ACATGAGCAA | 1620
| TTTATAGTAC | AGTGTCATAA | TGTTCGATCG | CAACCAAACA | AAGAGCAATT | TCATAGTTTT | 1680
| TACATGCGCC | TCATTATTCA | TAGAAGTATA | GTGGACATAA | GATCCTCGTC | ATTTTGCCC | 1740
| TGTTAGAACG | GATATCGAAG | CCTCCATGCT | CACTCTTTCG | TCGGCTTCTC | TTTATCATCC | 1800
| ACCTCCTTCT | TCACCTTTCC | CAACTTGACC | GTCAAGCACT | TCAAGATCCT | AACACGGACA | 1860
| GTTCTACGA | TTATTTTGC | ATCGTCATCC | AACACATTCA | TGTTCAAGGT | CAACATCTTT | 1920
| ATATCTTCCG | AAACGGTCGC | GAGCTCAACT | TGCTCATAGT | TTTTTAGGC | AGCAGAAGTT | 1980
| GGCCCGAAAC | TTTAAACCAA | ACACAGCGTA | AATTTACCAT | CATTACACCA | ATAATTGCCA | 2040
| TAAAAAATAT | TCCTATTTGA | TTTACTATGC | TTATTATTAA | AAATCCGACA | TTATATTTTT | 2100
| TTTTCTGTTC | ATGAGTCACA | ACTATTCCCT | TTTTTCAGA | CGGAAATCGC | AGTTATTGCC | 2160
| GACATACTAC | TAATGTCGAT | GTACACGGTC | CACATTTACC | GCCCAAGTTT | AATGTGACCG | 2220
| CACCTAAAGA | AAAGAAAAAG | TTAATGTCAC | CGCACACAGA | CGGACCCACC | TAACAGCTGG | 2280
| CCCACGCTGC | CTTCTATGCG | CCTTCCACGA | AGAAATCCGG | CCCCACCTGC | CGGTGACCCT | 2340
| CCAAGCACGT | CCCTATATAG | ACTTCCTCGT | GTGCGGCCAT | CTCGGTCTCT | CTCTCTCTCC | 2400
| TCCATTCCTC | TCTCCTCCTC | CTGCCACCGA | TCCCAAACCA | GGGAGGAACC | CGGCGCGAGG | 2460
| AGGGCAAAGG | AAGAGAAGAG | GAGACCACCC | AGCCGACCGC | GCGACCGCAC | GCACAGGGCA | 2520
| GCAGCCGTCG | CGATCCCGGT | AACCACCATT | CGCCGGATCT | CTCCTTCCCC | CGTCGCCCCT | 2580
| CCTGTGATCC | GATCGGTGGT | TTGGTCGCTC | GATTCGTCAT | ACTATTTTC | GTTGTTGTGA | 2640
| CCGGCTTCAC | CTGTTTAGTG | GTTCGGGTGT | GTTCGATCTC | ATCATCCTGT | CGGTGTCCGG | 2700
| TAGATTCGAT | CCGTTTCTCG | AGGGTGCGGC | TCGAGGAATC | TGCCGCGTTT | GACCGGCTTC | 2760
| GGTCGGCCCA | GCGTTGTTCT | CACGCGGGGT | GCTCGGGAAT | CCCGCGCGGA | GCCGGTCGCG | 2820
| AATCTGGTCC | GGTTTAGCGC | TGTTCGTGCG | CCGTGGCGTG | GATCTGGCGC | TGCTGCCCTC | 2880
| AGATCTTGTA | GATCTAGTTG | GGTGGCTTCA | ATTCTGGAGT | ATTTTTTTAT | TGTTGTTATT | 2940
| ATAGAACGAG | CCTGTGTCTG | TGTTGATCTA | TGGGTCTGAC | GCTTCGGCCT | TGAATTTGTT | 3000
| TCGTTTGATT | TCAGCGCAGG | AGCGGACATG | GGGCTCACGT | TCACTAAGCT | GTTCAGTCGG | 3060

CTCTTCGCCA AGAAGGAGAT GAGGATCC 3088

(2) INFORMATION FOR SEQ ID NO:2:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

ACGAATTCAT GGGGCTCACG TTTACCAAGC TG 32

(2) INFORMATION FOR SEQ ID NO:3:

(i) SEQUENCE CHARACTERISTICS:
        (A) LENGTH: 181 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Gly Leu Thr Phe Thr Lys Leu Phe Ser Arg Leu Phe Ala Lys Lys
 1           5                  10                  15

Glu Met Arg Ile Leu Met Val Gly Leu Asp Ala Ala Gly Lys Thr Thr
                20                  25                  30

Ile Leu Tyr Lys Leu Lys Leu Gly Glu Ile Val Thr Thr Ile Pro Thr
            35                  40                  45

Ile Gly Phe Asn Val Glu Thr Val Glu Tyr Lys Asn Ile Ser Phe Thr
        50                  55                  60

Val Trp Asp Val Gly Gly Gln Asp Lys Ile Arg Pro Leu Trp Arg His
 65                  70                  75                  80

Tyr Phe Gln Asn Thr Gln Gly Leu Ile Phe Val Val Asp Ser Asn Asp
                85                  90                  95

Arg Asp Arg Val Val Glu Ala Arg Asp Glu Leu His Arg Met Leu Asn
                100                 105                 110

Glu Asp Glu Leu Arg Asp Ala Val Leu Leu Val Phe Ala Asn Lys Gln
            115                 120                 125

Asp Leu Pro Asn Ala Met Asn Ala Ala Glu Ile Thr Asp Lys Leu Gly
        130                 135                 140

Leu His Ser Leu Arg Gln Arg His Trp Tyr Ile Gln Ser Thr Cys Ala
145                 150                 155                 160

Thr Thr Gly Glu Gly Leu Tyr Glu Gly Leu Asp Trp Leu Ser Ser Asn
                165                 170                 175

Ile Ala Asn Lys Ser
            180
```

(2) INFORMATION FOR SEQ ID NO:4:

(i) SEQUENCE CHARACTERISTICS:
        (A) LENGTH: 181 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Met Gly Asn Ile Phe Gly Asn Leu Leu Lys Ser Leu Ile Gly Lys Lys

|  | 1 |  |  |  | 5 |  |  |  |  | 10 |  |  |  |  | 15 |
|---|---|---|---|---|---|---|---|---|---|---|---|---|---|---|---|
|  | Glu | Met | Arg | Ile | Leu | Met | Val | Gly | Leu | Asp | Ala | Ala | Gly | Lys | Thr | Thr |
|  |  |  |  | 20 |  |  |  |  | 25 |  |  |  |  | 30 |  |  |
|  | Ile | Leu | Tyr | Lys | Leu | Lys | Leu | Gly | Glu | Ile | Val | Thr | Thr | Ile | Pro | Thr |
|  |  |  | 35 |  |  |  |  | 40 |  |  |  |  | 45 |  |  |  |
|  | Ile | Gly | Phe | Asn | Val | Glu | Thr | Val | Glu | Tyr | Lys | Asn | Ile | Ser | Phe | Thr |
|  |  | 50 |  |  |  |  | 55 |  |  |  |  | 60 |  |  |  |  |
|  | Val | Trp | Asp | Val | Gly | Gly | Gln | Asp | Lys | Ile | Arg | Pro | Leu | Trp | Arg | His |
|  | 65 |  |  |  |  | 70 |  |  |  |  | 75 |  |  |  |  | 80 |
|  | Tyr | Phe | Gln | Asn | Thr | Gln | Gly | Leu | Ile | Phe | Val | Val | Asp | Ser | Asn | Asp |
|  |  |  |  |  | 85 |  |  |  |  | 90 |  |  |  |  | 95 |  |
|  | Arg | Glu | Arg | Val | Asn | Glu | Ala | Arg | Glu | Glu | Leu | Met | Arg | Met | Leu | Ala |
|  |  |  |  |  | 100 |  |  |  |  | 105 |  |  |  |  | 110 |  |
|  | Glu | Asp | Glu | Leu | Arg | Asp | Ala | Val | Leu | Leu | Val | Phe | Ala | Asn | Lys | Gln |
|  |  |  |  | 115 |  |  |  |  | 120 |  |  |  |  | 125 |  |  |
|  | Asp | Leu | Pro | Asn | Ala | Met | Asn | Ala | Ala | Glu | Ile | Thr | Asp | Lys | Leu | Gly |
|  |  |  |  | 130 |  |  |  |  | 135 |  |  |  |  | 140 |  |  |
|  | Leu | His | Ser | Leu | Arg | His | Arg | Asn | Trp | Tyr | Ile | Gln | Ala | Thr | Cys | Ala |
|  | 145 |  |  |  |  | 150 |  |  |  |  | 155 |  |  |  |  | 160 |
|  | Thr | Ser | Gly | Asp | Gly | Leu | Tyr | Glu | Gly | Leu | Asp | Trp | Leu | Ala | Asn | Gln |
|  |  |  |  |  | 165 |  |  |  |  | 170 |  |  |  |  | 175 |  |
|  | Leu | Lys | Asn | Lys | Lys |  |  |  |  |  |  |  |  |  |  |  |
|  |  |  |  | 180 |  |  |  |  |  |  |  |  |  |  |  |  |

(2) INFORMATION FOR SEQ ID NO:5:

(i) SEQUENCE CHARACTERISTICS:
        (A) LENGTH: 181 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

|  | Met | Gly | Asn | Ile | Phe | Ala | Asn | Leu | Phe | Lys | Gly | Leu | Phe | Gly | Lys | Lys |
|---|---|---|---|---|---|---|---|---|---|---|---|---|---|---|---|---|
|  | 1 |  |  |  | 5 |  |  |  |  | 10 |  |  |  |  | 15 |  |
|  | Glu | Met | Arg | Ile | Leu | Met | Val | Gly | Leu | Asp | Ala | Ala | Gly | Lys | Thr | Thr |
|  |  |  |  | 20 |  |  |  |  | 25 |  |  |  |  | 30 |  |  |
|  | Ile | Leu | Tyr | Lys | Leu | Lys | Leu | Gly | Glu | Ile | Val | Thr | Thr | Ile | Pro | Thr |
|  |  |  | 35 |  |  |  |  | 40 |  |  |  |  | 45 |  |  |  |
|  | Ile | Gly | Phe | Asn | Val | Glu | Thr | Val | Glu | Tyr | Lys | Asn | Ile | Ser | Phe | Thr |
|  |  | 50 |  |  |  |  | 55 |  |  |  |  | 60 |  |  |  |  |
|  | Val | Trp | Asp | Val | Gly | Gly | Gln | Asp | Lys | Ile | Arg | Pro | Leu | Trp | Arg | His |
|  | 65 |  |  |  |  | 70 |  |  |  |  | 75 |  |  |  |  | 80 |
|  | Tyr | Phe | Gln | Asn | Thr | Gln | Gly | Leu | Ile | Phe | Val | Val | Asp | Ser | Asn | Asp |
|  |  |  |  |  | 85 |  |  |  |  | 90 |  |  |  |  | 95 |  |
|  | Arg | Glu | Arg | Val | Asn | Glu | Ala | Arg | Glu | Glu | Leu | Met | Arg | Met | Leu | Ala |
|  |  |  |  |  | 100 |  |  |  |  | 105 |  |  |  |  | 110 |  |
|  | Glu | Asp | Glu | Leu | Arg | Asp | Ala | Val | Leu | Leu | Val | Phe | Ala | Asn | Lys | Gln |
|  |  |  |  | 115 |  |  |  |  | 120 |  |  |  |  | 125 |  |  |
|  | Asp | Leu | Pro | Asn | Ala | Met | Asn | Ala | Ala | Glu | Ile | Thr | Asp | Lys | Leu | Gly |
|  |  |  |  | 130 |  |  |  |  | 135 |  |  |  |  | 140 |  |  |
|  | Leu | His | Ser | Leu | Arg | His | Arg | Asn | Trp | Tyr | Ile | Gln | Ala | Thr | Cys | Ala |
|  | 145 |  |  |  |  | 150 |  |  |  |  | 155 |  |  |  |  | 160 |
|  | Thr | Ser | Gly | Asp | Gly | Leu | Tyr | Glu | Gly | Leu | Asp | Trp | Leu | Ser | Asn | Gln |
|  |  |  |  |  | 165 |  |  |  |  | 170 |  |  |  |  | 175 |  |

Leu Arg Asn Gln Lys
             180

( 2 ) INFORMATION FOR SEQ ID NO:6:

( i ) SEQUENCE CHARACTERISTICS:
        ( A ) LENGTH: 181 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Met Gly Asn Val Phe Glu Lys Leu Phe Lys Ser Leu Phe Gly Lys Lys
  1               5                  10                  15
Glu Met Arg Ile Leu Met Val Gly Leu Asp Ala Ala Gly Lys Thr Thr
             20                  25                  30
Ile Leu Tyr Lys Leu Lys Leu Gly Glu Ile Val Thr Thr Ile Pro Thr
         35                  40                  45
Ile Gly Phe Asn Val Glu Thr Val Glu Tyr Lys Asn Ile Ser Phe Thr
     50                  55                  60
Val Trp Asp Val Gly Gly Gln Asp Lys Ile Arg Pro Leu Trp Arg His
 65                  70                  75                  80
Tyr Phe Gln Asn Thr Gln Gly Leu Ile Phe Val Val Asp Ser Asn Asp
                 85                  90                  95
Arg Glu Arg Val Asn Glu Ala Arg Glu Glu Leu Thr Arg Met Leu Ala
             100                 105                 110
Glu Asp Glu Leu Arg Asp Ala Val Leu Leu Val Phe Val Asn Lys Gln
             115                 120                 125
Asp Leu Pro Asn Ala Met Asn Ala Ala Glu Ile Thr Asp Lys Leu Gly
         130                 135                 140
Leu His Ser Leu Arg Gln Arg Asn Trp Tyr Ile Gln Ala Thr Cys Ala
145                 150                 155                 160
Thr Ser Gly Asp Gly Leu Tyr Glu Gly Leu Asp Trp Leu Ser Asn Gln
                 165                 170                 175
Leu Lys Asn Gln Lys
             180
```

( 2 ) INFORMATION FOR SEQ ID NO:7:

( i ) SEQUENCE CHARACTERISTICS:
        ( A ) LENGTH: 181 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Met Gly Asn Phe Ala Thr Asn Leu Phe Ser Asn Leu Phe Gly Asn Lys
  1               5                  10                  15
Glu Met Arg Ile Leu Met Val Gly Leu Asp Gly Ala Gly Lys Thr Thr
             20                  25                  30
Val Leu Tyr Lys Leu Lys Leu Gly Glu Val Ile Thr Thr Ile Pro Thr
         35                  40                  45
Ile Gly Phe Asn Val Glu Thr Val Gln Tyr Lys Asn Ile Ser Phe Thr
     50                  55                  60
Val Trp Asp Val Gly Gly Gln Asp Arg Ile Arg Ser Leu Trp Arg His
 65                  70                  75                  80
```

-continued

```
        Tyr  Tyr  Arg  Asn  Thr  Glu  Gly  Val  Ile  Phe  Val  Val  Asp  Ser  Asn  Asp
                            85                       90                      95

Arg  Ser  Arg  Ile  Gly  Glu  Ala  Arg  Glu  Val  Met  Gln  Arg  Met  Leu  Asn
                            100                      105                     110

Glu  Asp  Glu  Leu  Arg  Asn  Ala  Ala  Trp  Leu  Val  Phe  Val  Asn  Lys  Gln
                  115                           120                125

Asp  Leu  Pro  Glu  Ala  Met  Ser  Ala  Ala  Glu  Ile  Thr  Glu  Lys  Leu  Gly
                  130                      135                     140

Leu  His  Ser  Ile  Arg  Asn  Arg  Pro  Trp  Phe  Ile  Gln  Ala  Thr  Cys  Ala
        145                           150                 155                      160

Thr  Ser  Gly  Glu  Gly  Leu  Tyr  Glu  Gly  Leu  Glu  Trp  Leu  Ser  Asn  Ser
                            165                      170                     175

Leu  Lys  Asn  Ser  Thr
                            180
```

(2) INFORMATION FOR SEQ ID NO:8:

(i) SEQUENCE CHARACTERISTICS:
        (A) LENGTH: 52 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 5..52

(xi) SEQUENCE DESCRIPTION: SEQ ID NO:8:

```
GACC ATG  CCG  GTC  GAC  TCT  AGA  GGA  TCC  CCG  GGT  GGT  CAG  TCC  CTT  ATG              49
     Met  Pro  Val  Asp  Ser  Arg  Gly  Ser  Pro  Gly  Gly  Gln  Ser  Leu  Met
     1                   5                        10                      15

TTA                                                                                          52
Leu
```

(2) INFORMATION FOR SEQ ID NO:9:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:9:

```
Met  Pro  Val  Asp  Ser  Arg  Gly  Ser  Pro  Gly  Gly  Gln  Ser  Leu  Met  Leu
1                   5                        10                      15
```

GENE EXPRESSION VECTOR USING THE GENE EXPRESSION REGULATING REGION OF THE ADP RIBOSYLATION FACTOR

BACKGROUND OF THE INVENTION

1. Field of the Invention

This invention relates to the field of genetic engineering of plants, and more specifically, to regulation of gene expression using an gene expression regulating region of the ADP ribosylation factor gene in plants.

2. Description of the Related Art

Due to recent progress in genetic engineering, research on the plant breeding at the genetic level (so-called molecular plant breeding) is now being carried out intensively. In order to achieve a successful plant breeding, using genetic engineering techniques, the useful genes in the plants must be expressed and made to function to achieve a specific purpose efficiently. Generally, therefore, to regulate gene expression and achieve the desired purpose, a gene expression regulating region in the plant is isolated for use.

Typical gene expression regulating regions that have so far been used in this way are, for example, the 35 s promoter of the tobacco mosaic virus (Guilley, H., et al (1082), Cell 30, 763–773), and the actin gene promoter derived from rice plants (McElroy, D. et al, (1990), The Plant Cell, 2, 163–171).

However, the number of common multi purpose promoters in plants is still limited, and considering that time, place and degree of expression are also important in any plant that is to be modified, there are very few actual cases where the gene expression regulating region of a plant can actually be utilized. This is due to the fact that the technology, whereby useful genes that have been separated or manufactured for the plant breeding can be freely expressed and made to function in the plant, is not yet very advanced.

The establishment and accumulation of techniques for regulating gene expression in plants with a view to making useful genes function efficiently to serve a specific purpose, has therefore been long awaited.

SUMMARY OF THE INVENTION

This invention was conceived in order to resolve the above problems, and aims to construct a genetic expression vector that can express genes in a tissue-specific, efficient manner. More specifically, it aims to provide a gene expression vector that, using genetic engineering techniques, can express useful genes efficiently to serve a specific purpose in the plant breeding or the production of substances using plant tissues or cells.

In order to achieve the above aims, this invention features the use of the promoter of an ADP ribosylation factor as a plant promoter.

Still more specifically, this invention comprises a DNA fragment having a base pairs 1 to 3027 in SEQ ID NO: 1:, or a DNA fragment comprising part of this fragment having promoter activity.

This invention further comprises an expression vector comprising any of the aforesaid DNA fragment.

Still further, this invention comprises a transformant comprising any of the aforesaid expression vector.

By using the gene expression regulating region of this ADP ribosylation factor (referred to hereinafter as ARF) gene for the gene expression, a desired gene can be efficiently expressed in any plant of interest, and utilized for plant breeding and the production of useful substances using plant culture cells.

DETAILED DESCRIPTION OF THE INVENTION

[ADP ribosylation factor (ARF)]

(References)

ARF was first discovered as a enhancing factor for cholera toxin. In mammals, it is present in particularly large amounts in the brain, accounting for 1% of total protein (Kahn, R., and Gilman, A. G. (1984), The Journal of Biological Chemistry, 259, 6228–6234). According to recent research, ARF is a protein of molecular weight approximately 20 kD that commonly exists in eukaryotes, and is known to be a type of low molecular weight G protein that contributes to intracellular transport (Serafini, T., et al (1991) Cell, 67, 239–253). Its gene structure has been reported for yeast, mammals, and dicotyledons (Sewell, J. L., Proc. Natl. Acad. Sci. USA (1988) 85, 4620–4624).

(The Inventors' Research)

In the research aimed at constructing tissue-specific gene expression systems in barley. The inventors discovered that the ARF gene is characteristic in that it is actively expressed in barley seeds, roots and callus, but strongly suppressed or almost not expressed at all in the leaves.

The Inventors' research was the first of its kind to investigate ARF from the viewpoint of gene expression rather than that of function, and was also the first to show that the expression region of the ARF gene could be used as a vector of industrial utility. It is hoped that the expression vector constructed from the gene expression region of ARF according to this invention, will find wide application as a characteristic gene expression system for the plant breeding and production of substances using plant tissues or cells with the use of genetic engineering techniques.

[Isolation of cDNA of ARF]

The Inventors, using differential screening techniques, succeeded in cloning the cDNA of the ARF gene that is expressed tissue-specifically and at a high level, and isolating a full length cDNA. Next, by cloning the upstream region of the ARF gene, they verified its promoter activity, and created a gene expression vector using the gene expression regulating region of this gene.

[Acquisition of Expression Vector]

The Inventors screened the gene library of barley, isolated a DNA fragment in the upstream region of this gene, and combined this fragment with a reporter gene so as to construct an expression vector.

More specifically, a gene expression vector using the promoter of the ARF gene according to this invention may be obtained by the following methods.

(Differential Screening)

In general, expression-specific genes may be cloned from cells and tissues having different genetic expressions according to the method of Takahashi et al (Takahashi, Y., Kuroda, H. et al (1989), Proc. Natl. Acad. Sci. USA 86, 9279–9283). For example, after extracting polyA$^+$ RNA from roots, cDNA is synthesized, and the cDNA fragments are cloned into a lambda phage vector or plasmid vector to produce a cDNA library. Part of the library is subjected to plating, transferred to a nylon filter, and hybridized with a radioactive probe of leaves and roots. The clone which is expressed specifically in the roots is then screened. The sequence of bases in the clone may be determined by the usual methods.

(Cloning of Promoter)

General methods for cloning fragments in the upstream region of genes are given in detail in Sambrook, J., Frisch, E. F., Maniatis, T., Molecular Cloning, A Laboratory Manual (1989), Cold Spring Harbor Laboratory Press. According to this invention for example, as the base sequence of cDNA is well known, suitable restriction enzymes may be used to cleave chromosome DNA, and the genome Southern method used to determine the size of the fragments obtained in the upstream region. Next, barley chromosome DNA is separated, cleaved with these enzymes, and this DNA used to construct a chromosome library. If a radio-active cDNA probe is synthesized and this library is screened, a desired upstream region may be cloned.

(Verification of Function of Gene Expression Vector)

To determine whether the upstream region so obtained functions as a promoter, it is usual to ligate the upstream region to a reporter gene, introduce into a suitable cell or tissue, and verify the expression of the reporter gene by enzyme activity. The creation of precise gene fusions with reporter genes represents an elegant and powerful means of simplifying the problem. For example, delineation of the contribution of transcriptional control is effected by eliminating most or all of the protein coding sequences, including the specific signals for post-transcriptional modifications, and replacing them with sequences from a readily assayed reporter gene. The detailed method is described in, for example, Draper, J., et al, Plant Genetic Transformation and Gene Expression, A Laboratory Manual (1988), Blackwell Scientific Publications.

The function of the vector according to this invention was verified by introducing it into barley culture cell protoplast, and analyzing the resulting gene expression. An alternative procedure is to detect the presence of NPT-II using specific antibody and immunochemical detection techniques.

According to this invention, an upstream region DNA fragment that had been separated, was ligated to a β-glucuronidase gene, and introduced into barley culture cell protoplast.

pBI 101.1 (Jefferson et al., 1987) is a 'promoterless' GUS cassette in the Agrobacterium binary plasmid vector pBin 19 (Bevan, 1984). It consists of the GUS gene from pRAJ260 (functionally identical to pRAJ255; Jefferson et al., 1986) blunt-end ligated into a filled-in Asp718 (Kpn I) site of the pBin 19 polylinker (the same as the pUC 19 polylinker) but upstream of a 260 bp Sst I—Eco RI fragment containing the polyadenylation signal from the nopaline synthase gene of the A. tumefaciens Ti plasmid pTiT37 (Bevan et al., 1983b). This allows plant promoters to be easily cloned upstream of GUS using the polylinker and transferred to plants with all the advantages of the binary vector systems. This vector has a low copy number RK2 origin of replication, and confers kanamycin resistance, both in bacteria and in plants. It should be cautioned that while there are no 'spurious' ATG codons on the GUS fragment of this vector, any promoters cloned into the Hind III site may have problems with the ATG of the polylinker Sph I site (GCATGC).

There are three plasmids in the pBI 101 series designed specifically for translational fusions which allow the creation of fusion junctions in all three reading frames. pBI 101.2 and pBI 101.3 are plasmids resulting from the pBI 101.1 construction that provide the other two reading frames of GUS relative to the polylinker sites.

The oligonucleotide (5'-G-A-T-T-T-C-A-C-G-G-G-T-T-G-G-G-G-T-T-T-C-T-3';) is very useful for priming the DNA sequence analysis of GUS gene fusion junctions. This 22-base oligonucleotide is complementary to the GUS coding strand and terminates 14 bp downstream of the A of the initiator ATG. When constructing gene fusions, this primer can be successfully used for double-strand sequencing of miniprep DNA to confirm construction details. It is also useful for primer-extension analysis of chimaeric transcripts (Boulnois, 1987).

After several days culture, promoter function was verified by extracting total protein, and measuring enzyme activity in total protein using 4-methyl umbelliferyl glucuronide (4-MUG) as substrate. As a result, it was found that this DNA fragment may be used as a gene expression vector.

(Isolating Methods for DNA Fragments Which Code for ARF Promoter)

A DNA fragment having a base SEQ ID NO: 1: could be obtained by a method described below. First, synthetic PCR primers having the sequence corresponding to base sequence 1 to 50 and synthetic PCR primers having the sequence complementary to 2976 to 3027 are synthesized by DNA synthesizers, for example 391 DNA Synthesizer (ABI inc.) or Gene Assembler (Pharmacia inc.). A barley genomic DNA is purified by CTAB methods or SDS-phenol methods (fully described in Plant Genetic Transformation and Gene expression, Draper et al). Finally, DNA fragments having the base sequence of ARF promoter are synthesized by Polymerase Chain Reaction with use of, for example, LA PCR kit (Takara inc.) or XL-Wax100 (Perkin Elmer inc.).

Alternatively, DNA fragments having the base sequence of ARF promoter are synthesized directly. For example, synthetic DNA having the base sequence 1 to 110 of SEQ ID NO: 1: and synthetic DNA having the base sequence complementary to 1 to 16 are synthesized.

Double strand DNA having the base sequence 1 to 110 of SEQ ID NO: 1: is obtained by Klenow filling reaction with these primers. With a same method, a DNA fragment having the base sequence of 100 to 190 is obtained. Next, by a general molecular cloning method, these two DNA fragment is ligated by use of restriction enzyme ApaI which recognition site is located the sequence 104. Finally, a full length DNA fragment having the base sequence 1 to 3027 of SEQ ID NO: 1: is obtained by repeating procedure described above.

BRIEF DESCRIPTION OF THE DRAWINGS

FIG. 1 is a drawing showing the results, at the amino acid level, of a computer search of the homology between the cDNA clone R151 and the ARF gene in man, bovine and yeast (SEQ ID NOS:3–7). In the figure, — indicates common amino acid sequences, while the shading shows amino acids that are thought to be GTP binding sites.

FIG. 2 is a diagram of a restriction enzyme map of the clone λR15.

FIGS. 3 (a)–(e) are drawings showing the processes for constructing a gene expression vector (SEQ ID NOS:8–9).

DESCRIPTION OF THE PREFERRED EMBODIMENTS

Figure 4:
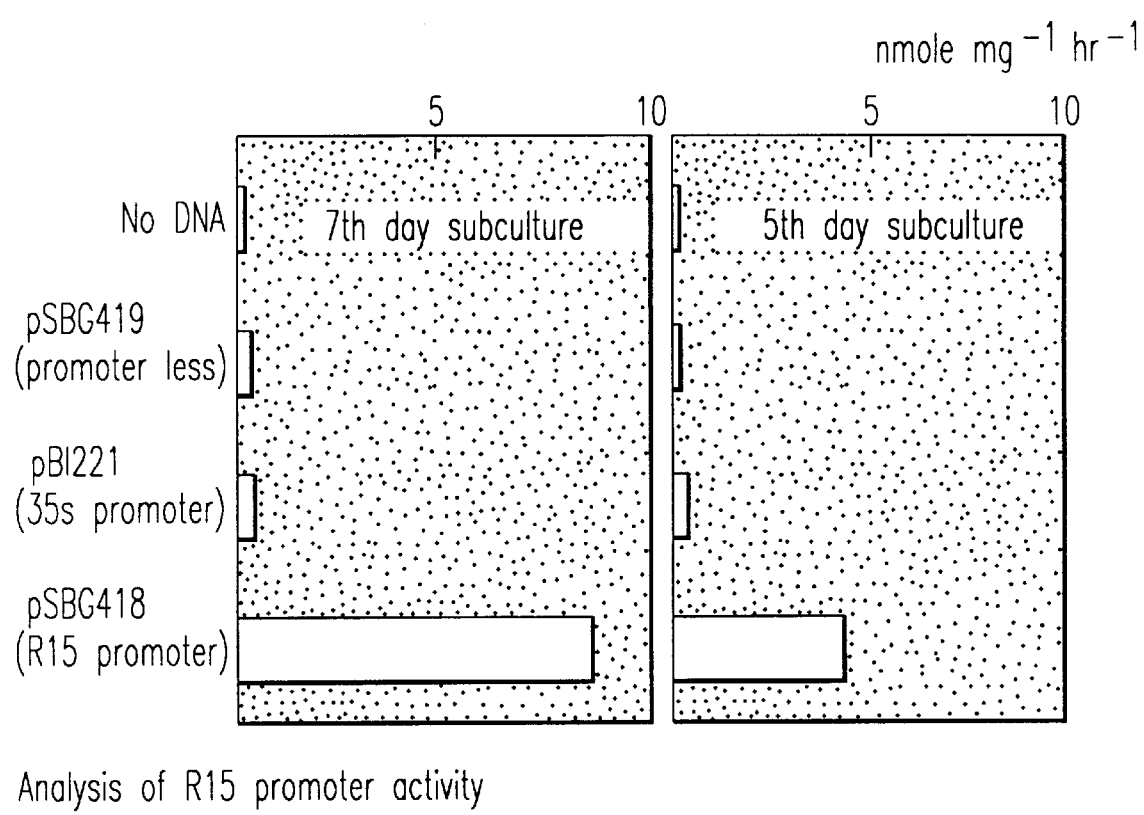
FIG. 4 is a drawing showing the results of a study of the activity of the promoter (R15 promoter (pSBG418)) according to this invention.

As described hereintofore, according to this invention, full length cDNA was isolated by differential screening. The gene library of barley was screened so as to isolate a DNA fragment in the upstream region of this gene, and this fragment was combined with a reporter gene so as to construct a gene expression vector. This vector was then introduced into the protoplast of barley culture cells, and its function was verified by analyzing genetic expression. The invention will now be described in further detail with reference to specific examples, however it is understood that the invention is not to be construed as being limited to them in any way.

EXAMPLE 1

Construction of the cDNA library expressed in roots

The roots(10 g) of young barley plants (cultivar Haruna Nijo) whereof the first and second leaves had opened was separated, frozen in liquid nitrogen and crushed to a powder in a blender in liquid nitrogen. After allowing the liquid nitrogen to evaporate, 100 ml of 4M guanidine isocyanate in 0.1M Tris-HCl (pH 7.0) and 100 ml of a phenol:chloroform:isoamyl alcohol mixture (25:24:1) were added, and the resulting mixture blended in the blender for several minutes. The suspension was transferred to a centrifuge tube, centrifuged at 4000×g for 20 min, and the aqueous layer recovered. To this an equal volume of the phenol:chloroform:isoamyl alcohol (25:24:1) mixture was added, the resulting mixture centrifuged, and the aqueous layer recovered. This procedure was repeated until the intermediate layer between the phenol layer and the water layer had disappeared, then 1/10 volume of 3M sodium acetate and 2.5 volumes of ethanol were added so to the aqueous layer as to precipitate total nucleic acids. After dissolving the precipitate in 10 ml 0.5M KCl/10 mM Tris-HCl (pH 8), polyA$^+$ RNA was purified using an oligo dT cellulose (Boehringer Inc.) column.

cDNA was synthesized from 2 μg of this polyA$^+$ RNA using a cDNA synthesis kit (Amersham Inc., cDNA synthesis system plus). A λgt10 library was then constructed using this cDNA and cDNA cloning system λgt10 (Amersham Inc.).

EXAMPLE 2

Differential screening

PolyA$^+$ RNA was purified from leaves of young barley plants whereof the first and second leaves had opened, using the method of Embodiment 1. After the λgt10 library constructed in Embodiment 1 was subjected to plating to give $10^3$ pfu/plate, it was transferred to a high bond N$^+$ filter (Amersham Inc.) and fixed with alkali. This was repeated twice so as to prepare two filters. The filters were hybridized with a radioactive cDNA probe ($10^5$ cpm/μg polyA$^+$ RNA), synthesized using 2 μg of polyA$^+$ RNA from roots and leaves respectively as a template, in 20 ml of hybridization solution (6×SSC, 1% SDS) at 65° C. for 24 hrs, and washed four times with a wash solution (2×SSC, 1% SDS) at 65° C. After drying the filters, an autoradiograph was performed, and the signal strength of each phage clone was compared. Clones that showed a strong signal in roots were recovered from the original plate.

EXAMPLE 3

Structural analysis of cDNA clones

Various phage clones were grown, and the DNA recovered. cDNA insert was separated from this DNA, and cloned with pUC118 or pUC119 (Takarashuzo Inc.). The base sequence was determined by the di-deoxy method using an ABI Inc. 373 ADNA sequencer.

EXAMPLE 4

Analysis of CDNA clone R151

Several CDNA base sequences were determined, and a computer search was performed. As a result, approximately 90% homology was found at the amino acid level between one of these, cDNA clone R151, and the ARF gene in man, bovine and yeast (FIG. 1). When this cDNA clone was used as a probe to perform a Northern blot analysis, it was found that this gene was very strongly expressed in barley seeds, roots and culture cells, but hardly at all in leaves.

EXAMPLE 5

Cloning of upstream DNA fragment

Genomic Southern was performed on barley chromosome DNA cleaved by the restriction enzyme HindIII, using an upstream DNA fragment containing an ARF protein N terminal region obtained by HindIII cleavage of this cDNA clone R151 as a probe. As a result, a 5 kb band was detected which could be cloned, and which is thought to contain a promoter region. Barley chromosome DNA was therefore cleaved by HindIII, DNA fragments near 5 kb separated by electrophoresis, and ligated to the HindIII site of Lambda Blue MidTM (Clontech Inc.) in order to construct a library. This library was screened by the above probe to obtain the clone λR15. In other words, according to this embodiment, a genomic library was screened using the HindIII upstream probe R151 so as to isolate λDNA.

EXAMPLE 6

Structural analysis of upstream DNA fragments

After cloning the above fragments at the HindIII site of pUC118, a restriction enzyme map was constructed (FIG. 2). Enzymes that do not cleave λR15 are EcoRI, ClaI, SalI, KpnI, NaeI, SacII, SmaI. As a result, from the restriction map of λR15, the N terminal of ARF protein is probably located effectively in the center, and its orientation is probably as shown in FIG. 2. To determine the precise position of the N terminus, a polymerase chain reaction (PCR) was performed using the synthetic primer 5'-ACGAATTCATGGGG CTCACGTTTACCAAGCTG-3' (SEQ ID NO:2) and M13 primer (Takarashuzo Inc.) that recognize base sequences coding the N terminus shown in Sequence Table 2, and the sizes of DNA fragments after reaction were determined. It was found that the N terminus is situated at approximately 2.3 kbp from downstream. The HindIII (1)—BamHI (3070) fragment corresponding to the upstream part containing near the N terminus was therefore cloned to pUC118 from near the N terminus, and the base sequences were determined by the method shown in the examples so as to obtain the results shown in Sequence Table 1.

EXAMPLE 7

Construction of gene expression vector, and expression analysis (Construction of gene expression vector)

The β-glucuronidase gene, which is a reporter gene, was ligated to the ARF promoter fragment, and promoter activity was measured. pBI101 shown in FIG. 3(a) (Toyobo Inc.) was cleaved by the restriction enzymes HindIII and EcoRI, a 2280 bps fragment was recovered by electrophoresis, then cloned into pUC118 at the HindIII and EcoRI sites to construct pSBG419 (FIG. 3(b)). Next, pSBG419 was cleaved by the restriction enzyme PstI, and self ligated after blunting using a Takarashuzo DNA blunting kit to construct pSBG420 (FIG. 3(c)). Using the same method, the upstream DNA fragment shown in Example 5 was cloned at the HindIII site of pSBG420 to construct pSBG421 (FIG. 3(d)). pSBG421 was then inserted into E. coli DH5 (Toyobo Inc.) by the usual method. pSBG421 was cleaved by the restriction enzymes XhoI and SphI, and cloned with the fragment XhoI (2700)—NiaIII (3010) shown in the Sequence Table I to construct pSBG418 (FIG. 3(e)). pSBG418 has a structure wherein a β-glucuronidase fused gene, comprising the genes for the amino acids methionine, proline, valine, asparagine, serine, alginine, glycine, serine, proline, glycine, glycine, glutamine, serine and leucine which are attached to an N terminus downstream of the ARF promoter, is linked. Transcription of the β-glucuronidase fused gene is induced by the action of the ARF promoter.

(Expression analysis)

Next, a transient expression test was performed using the protoplast of a suspension culture B53 derived from the immature embryo of wild barley (from Hordeum bulbosum), and promoter activity was examined (FIG. 4). Using enzyme solutions, approximately $10^8$ protoplasts were isolated from cell suspension on the 5th or 7th day of subculture. To the protoplasts resuspended (2 ×$10^6$) were added 2 nmol pSBG418, pBI221 (Toyobo Inc.) and calf thymus DNA as carrier DNA so that the total was 60 λg, and electroporation was performed using a Biorad gene pulser at 900 V/cm and 125 μF. After recovering the protoplasts, they were suspended in 15 ml of MSD4, 0.6M mannitol, and cultured in a 9-cm Petri dish at 25° C. for 3 days. After culture, the cells were recovered, solubilized in Gus extract buffer (50 mM phosphate buffer (pH 7.0), 10 mM EDTA (pH 7.0), 0.1% Triton X-100, 0.1% sodium lauryl sarcosine, 10 mM mercaptoethanol), and a GUS assay was performed on 100 μg of soluble protein using substrate 4MUG.

The samples showed specific activities of 8.9 nmol 4-MUmg$^{-1}$hr$^{-1}$ soluble protein and 0.3 nmol 4-MUmg$^-$ $_1$hr$^{-1}$ soluble protein respectively. It is therefore clear that the promoter of this invention (R15 promoter (pSBG418)) shows a higher activity, for both the 5th and 7th day subcultures, than the 35 s promoter (pBI221) that has been used conventionally. In particular, the 7th day subculture shows approximately 30 times the activity of the 35 s promoter.

If it is desired to express other useful genes, these useful genes may be inserted instead of the β-glucuronidase fusion gene. This can easily be accomplished using known, common techniques by those skilled in the art.

Advantages of the Invention

As described hereintofore, the gene expression vector constructed using the ARF gene expression region according to this invention, has wide application as a characteristic gene expression system in the plant breeding and in the production of substances using plant tissues or cells with the use of genetic engineering techniques. The gene expression vector employing the gene expression regulating region in the AFR gene of this invention, therefore, makes a significant contribution to efficiently expressing a desired gene in a plant for a specific purpose, improving plant species, and producing useful substances using plant culture cells.

What is claimed is:

1. A DNA fragment having a base sequence 1 to 3027 of SEQ ID NO:1.

2. An expression vector comprising a DNA fragment as defined in claim 1.

3. A transformant comprising an expression vector as defined in claim 2.

4. The DNA fragment of claim 1, wherein said fragment comprises a part of the base sequence 1 to 3027 of SEQ ID NO: 1 having promoter activity wherein said fragment exhibits a promoter activity of at least approximately 10 times the activity of a 35S promoter wherein said activity is measured by expression of β-glucuronidase in barley protoplasts.

5. A method of expressing genes in plants, comprising
    a) preparing an expression vector by operatively linking a gene whose expression is desired to the DNA fragment of claim 1, in a position 3' and in proper reading frame with said DNA fragment; and
    b) transforming plant cells with said expression vector.

6. A method of expressing genes in plants, comprising
    a) preparing an expression vector by operatively linking a gene whose expression is desired to the DNA fragment of claim 5, in a position 3' and in proper reading frame with said DNA fragment; and
    b) transforming plant cells with said expression vector.

7. The DNA fragment of claim 1, wherein said fragment comprises a part of the base sequence 1 to 3027 of SEQ ID NO: 1 having promoter activity, wherein said promoter activity is measured as approximately 3 to 10 nmol 4MU $mg^{-1}$ $hr^{-1}$ β-glucuronidase in barley protoplasts.

\* \* \* \* \*